United States Patent [19]

Nishiyama et al.

[11] 4,368,340
[45] Jan. 11, 1983

[54] PROCESS FOR PRODUCING 1,3,5-TRICHLOROBENZENE

[75] Inventors: Ryuzo Nishiyama, Takatsuki; Kanichi Fujikawa, Moriyama; Isao Yokomichi, Moriyama; Itaru Shigehara, Moriyama; Mikio Miyaji, Shiga, all of Japan

[73] Assignee: Ishihara Sangyo Kaisha Ltd., Osaka, Japan

[21] Appl. No.: 213,013

[22] Filed: Dec. 4, 1980

[30] Foreign Application Priority Data

Dec. 25, 1979 [JP] Japan .................... 54-168575

[51] Int. Cl.³ ............................ C07C 17/12
[52] U.S. Cl. ...................... 570/207; 570/202; 570/255; 570/260
[58] Field of Search ........... 570/202, 207, 252, 255, 570/260

[56] References Cited

U.S. PATENT DOCUMENTS 2,866,829  12/1958  Woodruff ............... 570/202
4,158,674  6/1979   Morris .................. 570/207
4,306,103  12/1981  Volkwein et al. ........ 570/207 X

FOREIGN PATENT DOCUMENTS 2920173   5/1979  Fed. Rep. of Germany ...... 570/207
54-112827 7/1979  Japan .
2067190   7/1981  United Kingdom ............ 570/207

OTHER PUBLICATIONS

Chemical Abstracts, vol. 92, No. 5, Feb. 4, 1980, Re. 41536x, p. 745.

Primary Examiner—Curtis R. Davis
Assistant Examiner—Asokkumar Pal
Attorney, Agent, or Firm—Oblon, Fisher, Spivak, McClelland & Maier

[57] ABSTRACT 1,3,5,-Trichlorobenzene is produced by chlorinating 1,3,5-trihalobenzene having 1 to 3 bromine atom and 2 to 0 chlorine atom. The gaseous 1,3,5-halobenzene having 1 to 3 bromine atom and 2 to 0 chlorine atom is brought into contact with chlorine gas at a molar ratio of 0.5 to 3.0 of the stoichiometric amount of chlorine required for said conversion, in a vapor phase at a temperature of 280° to 500° C.

6 Claims, No Drawings

PROCESS FOR PRODUCING 1,3,5-TRICHLOROBENZENE

BACKGROUND OF THE INVENTION

1. Field of the Invention

The present invention relates to an industrially advantageous process for producing 1,3,5-trichlorobenzene. More particularly, it relates to a process for producing 1,3,5-trichlorobenzene by chlorinating bromine-containing trihalobenzene (substitution of bromine atom with chlorine atom) in a vapor phase.

2. Description of the Prior Arts 1,3,5-Trichlorobenzene is important for industrial organic syntheses and it has been recently considered to be important as the starting material for explosives and various fine chemicals. It has been required to find an industrial process for production thereof.

Heretofore, 1,3,5-trichlorobenzene has been produced by various processes. For example, it has been proposed to produce 1,3,5-trichlorobenzene by isomerizing 1,2,4-trichlorobenzene in the presence of aluminum chloride and water at a refluxing temperature of 205° to 212° C. for 16 to 24 hours in U.S. Pat. No. 2,866,829. In this process, the condition of the reaction as the liquid phase reaction has been too severe and only about twenty and several % of 1,3,5-trichlorobenzene as the object compound has been obtained even though the reaction is continued for such long time. Moreover, the separation of the object compound from the reaction mixture has not been easy to be disadvantageous as the industrial process.

It has been proposed to produce 1,3,5-trichlorobenzene by chlorinating 1-bromo-3,5-dichlorobenzene in the presence of a catalyst of an azobisnitrile type compound or a benzoyl type compound in the liquid phase at about 65° to 100° C. in Japanese Unexamined Patent Publication 112827/1979. However, it has taken about 3 hours to complete this reaction. Moreover, a large excess of chlorine such as about 3 times of stoichiometrical amount of chlorine has been required and the catalysts are explosive to be dangerous. In the recovery of expensive bromine, it has required the complicated operations. Furthermore, the product has been contaminated by the catalyst or its decomposed material. These disadvantages have been found. In this process, bromine component is produced in a form of BrCl gas. In order to recover it as $Br_2$, it has been required to produce $Br_2$ by reacting chlorine gas with NaBr which is produced by reacting BrCl with an aqueous solution of NaOH. Moreover, $Br_2$ is contaminated with a small amount of the catalyst or its decomposed product to cause the adverse effect to the following isomerization for producing 1-bromo-3,5-dichlorobenzene as the starting material.

SUMMARY OF THE INVENTION

It is an object of the present invention to provide an industrially advantageous process for producing 1,3,5-trichlorobenzene. It is another object of the present invention to provide a process for producing 1,3,5-trichlorobenzene without a catalyst by a simple purification step in the condition suitable for an industrial operation.

The other object of the present invention is to provide a process for producing 1,3,5-trichlorobenzene in high yield for a short reaction time.

The further object of the present invention is to provide a process for recovering $Br_2$ having less impurity by a simple recovery step in the recovery of expensive bromine.

The foregoing and other objects of the present invention have been attained by providing a process for producing 1,3,5-trichlorobenzene which comprises reacting 1,3,5-trihalobenzene having 1 to 3 bromine atom and 2 to 0 chlorine atom with chlorine gas at a molar ratio of 0.5 to 3.0 times of the stoichiometric amount in the vapor phase at a temperature of 280° to 500° C.

DETAILED DESCRIPTION OF THE PREFERRED EMBODIMENTS

In accordance with the present invention, bromine atom is preferably substituted by chlorine atom by the chlorination of 1,3,5-bromobenzene or bromochlorobenzenes in a vapor phase under a specific condition for reaction to produce 1,3,5-trichlorobenzene.

(1) The reaction for substituting bromine atom by chlorine atom in a chlorination in a vapor phase has not been known in a prior art as an experiment or an industrial example.

(2) When 1,3,5-trichlorobenzene is further chlorinated in a vapor phase under the same condition to substitute remained hydrogen atom with chlorine atom, the reactivity is remarkably low whereby the by-production of an excess chlorinated products having 4 or more of chlorine atoms is negligible.

On the contrary, if monochlorobenzene or dichlorobenzene is chlorinated in a vapor phase, large amounts of trichlorobenzene isomers other than the object product and the excess chlorinated products are disadvantageously produced.

In accordance with the process of the present invention, 1,3,5-trichlorobenzene is selectively produced in high yield in view of the above-mentioned facts (1) and (2).

1,3,5-Bromobenzene or bromochlorobenzenes are 1,3,5-trihalobenzene having 1 to 3 bromine atom and 2 to 0 chlorine atom such as 1-bromo-3,5-dichlorobenzene, 1-chloro-3,5-dibromobenzene and 1,3,5-tribromobenzene. It is especially advantageous for an industrial process to use 1-bromo-3,5-dichlorobenzene because the content of bromine component is small to be the mild condition of reaction and to require the recovery of less bromine component.

The process of the present invention is superior to the conventional processes to provide the following industrial advantages.

(1) In the vapor phase chlorination, the substitution of bromine atom by chlorine atom is performed in substantially stoichiometrical conversion whereby the production of the by-products is small and the separation of the object compound of 1,3,5-trichlorobenzene is easy and the yield of the object compound is high.

(2) The reaction time is remarkably short and the reactor can be compact and the reaction can be continuous.

(3) In the reaction, bromine is produced in a form of $Br_2$ whereby $Br_2$ can be recovered by distilling the reaction mixture containing bromine and the chlorinated products in an industrial process. The resulting $Br_2$ does not contain impurities for adversely affecting to the following isomerization.

(4) Any dangerous catalyst is not used and the conventional reactor and purification and separation means can be used.

1,3,5-Bromobenzene or bromochlorobenzenes as the starting material are easily available or can be easily produced by the following industrial process.

(1) Bromine is added to dichlorobenzene, monochlorobenzene or benzene in the presence of an aluminum halide at a molar ratio of 0.003 to 0.1 based on the halobenzene at 0° to 180° C. to produce monobromodichlorobenzene, monochlorodibromobenzene or tribromobenzene.

(2) The resulting product is heated in the presence of an aluminum halide at a molar ratio of 0.03 to 1.0 based on the halobenzene at 80° to 180° C. for 1 to 5 hours to perform an isomerization of the trihalobenzene having bromine atom and a disproportionation.

(3) 1,3,5-Trihalobenzene having bromine atom is separated from the reaction mixture at a ratio of 10 to 40% and a part or the whole of the remained isomers of trihalobenzenes having bromine atom and the halobenzenes obtained by the disproportionation are returned into the step (1) or (2).

In accordance with the production of 1,3,5-trihalobenzene having bromine atom as the starting material, the following industrial advantages are given as well as the advantageous effects by the vapor phase bromine-chlorine substitution.

(a) In comparison with the process of U.S. Pat. No. 2,866,829, the condition of reaction such as the reaction temperature and the reaction time in the isomerization process is mild and a large amount of 1,3,5-trihalobenzene having bromine atom as the object compound is produced and the separation is easy to be high yield of 1,3,5-trihalobenzene having bromine atom.

(b) The residue remained by separating the object compound is recycled in the isomerization process whereby losses of the expensive bromine and other components are small.

(c) The vapor phase chlorination is continuously performed for a short time in substantially stoichiometrical reaction, whereby the reaction time is short and the adverse effect for the yield of the object product is small in comparison with those of the isomerization process. Therefore, the advantages of the isomerization process highly relate to the advantages of the process of the present invention over those of U.S. Pat. No. 2,866,829.

The chlorination of the present invention is carried out by the vapor phase reaction of 1,3,5-trihalobenzene having bromine atom with chlorine at 280° to 500° C.

In the vapor phase bromine-chlorine substituting reaction of the present invention, it is possible to use an inert organic solvent such as carbon tetrachloride and tetrachlorodifluoroethane or an inert gas such as nitrogen and helium as a diluent.

In usual, 1,3,5-trihalobenzene having bromine atom, chlorine gas and the diluent are fed into the reactor separately or as a mixture if necessary after preheating them. In the operation, 1,3,5-trihalobenzene having bromine atom is vaporized by directly heating it or by heating a solution obtained by dissolving it in an inert organic solvent, and the vaporized one can be fed into the reactor.

The vapor phase chlorination can be carried out in the reactor in which an inert solid filler is not packed, or in which an inert solid filler is packed in a form of a fixed bed or a fluidized bed as the reaction zone.

The amount of chlorine in the vapor phase chlorination is depending upon the kinds of the starting materials, the reactor and the condition of reaction and is not critical and is usually in a range of 0.5 to 3.0 preferably 0.8 to 2.0 molecular of that theoretically required for the chlorine substitution which is the amount theoretically required to convert 1,3,5-trihalobenzene having bromine atom to 1,3,5-trichlorobenzene by substituting all of bromine atoms by chlorine atoms. For example, when 1 mol of 1-bromo-3,5-dichlorobenzene is used as the starting material, 0.25 to 1.5 mol preferably 0.4 to 1.0 mol of chlorine is used.

The reaction temperature is not critical as the amount of chlorine and it is usually in a range of 280° to 500° C. preferably 300° to 400° C. The residence time of the reaction mixture in the reaction zone is not critical and it is usually in a range of 1 to 60 seconds.

In accordance with the vapor phase reaction, bromine atoms in 1,3,5-trihalobenzene having bromine atom are effectively substituted by chlorine atoms to produce 1,3,5-trichlorobenzene. The resulting 1,3,5-trichlorobenzene has low reactivity to further chlorination under the condition of reaction whereby the by-production of the excess chlorinated products having 4 or more of chlorine atoms is small to selectively produce 1,3,5-trichlorobenzene.

When the amount of chlorine and the reaction temperature are out of said ranges, the starting materials and the intermediates are disadvantageously recovered at high ratios or the excess chlorinated products and the carbonized products as the by-products are disadvantageously produced at high ratios.

The reaction mixture discharged from the reactor usually include chlorinated products and bromine ($Br_2$) whereby most of bromine can be recovered as $Br_2$ by a distillation in an industrial process.

The chlorinated products containing a small amount of bromine can be washed in an alkaline aqueous solution of sodium thiosulfate or sodium hydroxide and are separated by a phase separation under heating and the oily product is solidified by cooling at room temperature. The solid product comprises 80 to 98% of 1,3,5-trichlorobenzene as the object product, less than 20% of excess chlorinated products such as tetrachlorobenzene and less than 20% of the intermediates and the unreacted starting materials. The solid product is treated by the conventional separation and purification such as washing, distillation and crystallization, whereby 1,3,5-trichlorobenzene is easily separated to obtain 1,3,5-trichlorobenzene having a purity of higher than 98% in an yield of higher than 90%. The separated excess chlorinated products, the intermediates and the unreacted starting material, 1,3,5-trihalobenzene having bromine atom, are recycled into the vapor phase chlorination step.

On the other hand, bromine obtained by the reaction as the by-product can be recovered in high yield by the simple operation as described above and any impurity as the catalyst disclosed in Japanese Unexamined Patent Publication No. 112,827/1979 is not included. The recovered bromine can be used for the production of 1,3,5-trihalobenzene having bromine atom. Therefore, the industrial advantages are further increased by the combination of the process of the present invention with the process for producing 1,3,5-trihalobenzene having bromine atom by the bromination, and the isomerization.

The present invention will be illustrated by certain examples and references which are provided for purposes of illustration only and are not intended to be limiting the invention.

EXAMPLE 1

Isomerization step:

Monochlorodibromobenzenes were produced by gradually heating a mixture of 34 g. of monochlorobenzene and 0.4 g of aluminum chloride to 70° to 80° C. and adding dropwise 86.4 g. of bromine during 1 hour. After the addition of bromine, 15 g. of aluminum chloride was added to the reaction mixture and the mixture was heated at 130° C. to perform an isomerization for 2 hours. The reaction mixture was cooled and poured into water and washed to obtain a crude oily product. The oily product comprised 29.0% of 1-chloro-3,5-dibromobenzene, 34.6% of other monochlorodibromobenzenes, 23.6% of monobromomonochlorobenzene and 12.7% of monochlorotribromobenzene. The oily product was distilled under a reduced pressure of 60 mmHg at 165° to 170° C. to separate it into an initial fraction, a main fraction and a later fraction. The main fraction was cooled to room temperature or lower to crystallize it and the solid product was filtered to obtain 13 g. of solid 1-chloro-3,5-dibromobenzene.

A mixture of 17 g. of the initial fraction containing monobromomonochlorobenzenes as the main components and 37 g. of the filtrate containing monochlorodibromobenzene as the main component and 7 g. of the later fraction containing monochlorotribromobenzene as the main component was admixed with 6 g. of monochlorobenzene and 0.4 g. of aluminum chloride and then, 17 g. of bromine was added to perform the bromination, the isomerization and the purification by the same steps to obtain 13 g. of solid 1-chloro-3,5-dibromobenzene.

Vapor phase chlorination step:

A reactor equipped with a lateral reaction tube (diameter of 4 cm, length of 50 cm), a vaporizer and a preheating tube which are capabe of outward temperature control, was used and 1 mol of chlorine gas preheated at 300° C. was fed into the reaction tube and a solution of 1 mol of 1-chloro-3,5-dibromobenzene in 5 mol of carbon tetrachloride was preheated at 300° C. to vaporize it and the vapor was fed into the reaction tube during 50 minutes to react them at 340° C. The residence time of the reaction mixture was about 50 seconds.

The discharged gas from the reaction tube was fed into an alkaline aqueous solution of sodium thiosulfate to collect the reaction product. The phase separation was carried out at room temperature and carbon tetrachloride was distilled off to obtain oily product. The oily product was distilled to obtain 165 g. of 1,3,5-trichlorobenzene in yield of 91%.

EXAMPLE 2

In the reactor of Example 1, each chlorination of 1-bromo-3,5-dichlorobenzene (referring to as 3,5-CB) was carried out under the specific conditions of reaction. Each reaction mixture was collected to obtain each oily product and the oily product was distilled to obtain 1,3,5-trichlorobenzene as the object product (referring to as 1,3,5-TCB). The results are shown in Table 1.

In Process No. 1, 1-bromo-3,5-dichlorobenzene was heated at 300° C. without a diluent and the vaporized gas was directly fed into the reaction tube. In Process No. 2, 1 mol 1-bromo-3,5-dichlorobenzene was dissolved into 2.5 mol of carbon tetrachloride and the solution was heated at 250° C. to vaporize it and the vaporized gas was fed with 5 mol of nitrogen gas into the reaction tube.

TABLE 1

| Process | No. 1 | No. 2 |
|---|---|---|
| Starting material (mol) | | |
| 3,5 CB | 1.5 | 1 |
| Cl$_2$ | 0.97 | 0.75 |
| Condition of reaction | | |
| Reaction temp. (°C.) | 360 | 300 |
| Residence time (sec.) | 15.1 | 30 |
| Reaction time (hour) | 1 | 1 |
| Oily product: (%) | | |
| 1,3,5-TCB | 98.0 | 84.9 |
| 3,5-CB | 0.4 | 14.4 |
| Tetrachlorobenzene | 1.7 | 0.2 |
| Yield of 1,3,5-TCB(g.) | 263 | 145 |
| Percent yield of 1,3,5-TCB (%) | 96.6 | 79.9 |

EXAMPLE 3

In the reactor of Example 1, each chlorination of 1-bromo-3,5-dichlorobenzene was chlorinated under the specific condition.

The starting materials were respectively preheated at 300° C. and 1-bromo-3,5-dichlorobenzene was fed at a rate of 7.7 g./min. and chlorine was fed at a rate of 550 ml./min. into the reactor. The reaction was continuously carried out at a reaction temperature of 360° C. and a residence time of 14 seconds for 2 hours. The reaction mixture was cooled to collect 1029 g. of the mixture. The reaction mixture was distilled to recover 263 g. of bromine (recovery percent of 84%). The residue contained the object product and a small amount of bromine and it was washed in an aqueous solution of sodium thiosulfate and the product was separated under heating it by a phase separation to obtain 722.5 g. of 1,3,5-trichlorobenzene as the object product (yield of 97.2%).

EXAMPLE 4

Isomerization step:

In accordance with the process of Example 1 under the conditions shown in Table 2-1, the bromine was added dropwise to the mixture of dichlorobenzene (referring to as DCB) and aluminum chloride to produce monobromodichlorobenzenes (referring to as MBDCB) and then, aluminum chloride was added and the mixture was heated to attain the isomerization. The reaction mixture was cooled and washed with water to obtain crude oily products shown in Table 2-2. The crude oily products were respectively distilled at 130° to 137° C. under a reduced pressure of 60 mmHg. to obtain the main fraction. The product was solidified and filtered to obtain the solid 1-bromo-3,5-dichlorobenzenes (referring to as 3,5-CB). The initial fraction and the later fraction respectively contained dichlorobenzenes or dibromodichlorobenzene referring to as DBDCB as the main component. The results of the first reaction are shown in Table 2-2.

The total residues as the filtrate, the initial fraction and the later fraction were recycled to mix them with new starting materials to carry out the next reaction. The process was repeated. Certain examples of the reactions in the normal states are shown in Table 2-3 and the results are shown in Table 2-4.

TABLE 2-1

| | (First reaction) | |
|---|---|---|
| Process | No. 1 | No. 2 |
| Kind of DCB | p-dichloro-benzene | m-dichloro-benzene |
| Amount of DCB (g.) | 100 | 100 |
| Condition of reaction | | |
| Amount of aluminum chloride (initial one + additional one) (g.) | 4 + 20 | 4 + 20 |
| Addition of $Br_2$ (g.) | 87 g. | 87 g. |
| Temperature (°C.) and time for addition (hr.) | 60–70° C. 1 hour | 20–30° C. 1 hour |
| Temp. for heating (°C.) | 169 to 165 | 140 to 150 |
| Reaction time from addition of $Br_2$ (hours) | 6 | 5 |

TABLE 2-2

| | (First reaction) | |
|---|---|---|
| Process | No. 1 | No. 2 |
| Crude oily product | | |
| Yield (g.) | 140 | 142 |
| Composition (%) | | |
| 3,5-CB | 33 | 49 |
| DCB | 15 | 10 |
| MBDCB | 32 | 23 |
| DBDCB etc. | 20 | 18 |
| Yield of Initial fraction (g.) | 20 | 14 |
| Yield of main fraction (g.) | | |
| 3,5-CB(object comp.) (g.) | 32 | 50 |
| filtrate (g.) | 59 | 49 |
| Yield of later fraction (g.) | 23 | 25 |

TABLE 2-3

| | (Reaction in normal state) | |
|---|---|---|
| Process | No. 1 | No. 2 |
| Kind of DCB | p-dichloro-benzene | m-dichloro benzene |
| Amount of DCB (g.) | 13 | 35 |
| Amount of redives (g.) | 80 | 94 |
| Condition of reaction | | |
| Amount of aluminum chloride (initial one + additional one) (g.) | 2 + 20 | 2 + 20 |
| Addition of $Br_2$ (g.) | 13.5 g. | 30 g. |
| Temperature (°C.) and Time for addition (hr.) | 40–50° C. 0.5 hr. | 20–30° C. 0.5 hr. |
| Temp. for heating (°C.) | 160–165° C. | 140–150° C. |
| Reaction time from addition of $Br_2$ (hour) | 5 | 4 |

TABLE 2-4

| | (Reaction in normal state) | |
|---|---|---|
| Process | No. 1 | No. 2 |
| Crude oily product | | |
| Yield (g.) | 97 | 141 |
| Composition (%) | | |
| 3.5-CB | 30 | 42 |
| DCB | 23 | 10 |
| MBDCB | 36 | 30 |
| DBDCB etc. | 11 | 18 |
| Yield of Initial fraction (g.) | 24 | 15 |
| Yield of main fraction | | |
| 3.5-CB(object comp.) (g.) | 16 | 45 |
| filtrate (g.) | 45 | 53 |
| Yield of later fraction (g.) | 10 | 26 |

Vapor phase chlorination step:

In the reactor of Example 1, 1-bromo-3,5-dichlorobenzene obtained by the isomerization in the normal state was chlorinated in a vapor phase under the specific condition of reaction and the reaction product was collected to obtain an oily product and the oily product was distilled to obtain 1,3,5-trichlorobenzene as the object product. The results are shown in Table 2-5.

In Process No. 1, 1-bromo-3,5-dichlorobenzene was heated at 300° C. without a diluent and the vaporized gas was directly fed into the reaction tube. In Process No. 2, 1 mol of 1-bromo-3,5-dichlorobenzene was dissolved into 2.5 mol of carbon tetrachloride and the solution was heated at 250° C. to vaporize it and the vaporized gas was fed with 5 mol of nitrogen gas into the reaction tube.

TABLE 2-5

| Process | No. 1 | No. 2 |
|---|---|---|
| Starting material (mol) | | |
| 3,5-CB | 1.5 | 1 |
| $Cl_2$ | 1.05 | 0.75 |
| Condition of Reaction | | |
| Reaction temp. (°C.) | 350 | 400 |
| Residence time (sec.) | 18.1 | 25 |
| Reaction time (hours) | 1 | 1 |
| Oily product (%) | | |
| 1,3,5-TCB | 97.3 | 90.5 |
| 3,5-CB | 1.2 | 0 |
| Tetrachlorobenzene | 1.5 | 9.5 |
| Yield of 1,3,5-TCB (g.) | 260 | 155 |
| Percent yield of 1,3,5-TCB (%) | 95.5 | 85.4 |

EXAMPLE 5

Isomerization step:

In accordance with the process of Example 1 under the condition shown in Table 3-1, bromine was added dropwise to a mixture of benzene and aluminum chloride to produce tribromobenzene and then, aluminum chloride was added and the mixture was heated to attain the isomerization. The reaction mixture was cooled and washed with water to obtain crude oily products shown in Table 3-2. The crude oily product was distilled under a reduced pressure to obtain the main fraction containing tribromobenzene (referring to as TBB) as the main product. The product was solidified to obtain solid 1,3,5-tribromobenzene. The initial fraction contained monobromobenzene (referring to as MBB) and dibromobenzene (referring to as DBB) as the main components and the later fraction contained tetrabromobenzene (referring to as TEBB) as the main component. The results of the first reaction are shown in Table 3-2.

The total residues as the filtrate, the initial fraction and the later fraction were recycled to mix them with new starting materials to carry out the next reaction. The example of the second reaction is shown in Table 3-3 and the results are shown in Table 3-4.

TABLE 3-1

| (First reaction) | |
|---|---|
| Amount of benzene (g.) | 15.6 |
| Condition of reaction: | |
| Amount of aluminum chloride (initial one + additional one) (g.) | 0.2 + 15 |
| Amount of $Br_2$ (g.) | 90 g. |
| Temperature (°C.) | 80–100° C. |

TABLE 3-1-continued (First reaction)

| | |
|---|---|
| Time for addition (hr.) | 1 hour |
| Temp. for heating (°C.) | 130–135° C. |
| Reaction time from addition of $Br_2$ (hour) | 3 |

TABLE 3-2

(First reaction)

| | |
|---|---|
| Crude oily product: | |
| Yield (g.) | 60 |
| Composition (%) | |
| 1,3,5-TBB | 32.9 |
| 1,2,4-TBB | 32 |
| 1,2,3-TBB | 0.6 |
| MBB | 0.5 |
| DBB | 19.7 |
| TEBB | 14.3 |
| Yield of Initial fraction (g.) | 12 |
| Yield of main fraction (g.) | |
| 1,3,5-TBB (g.) | 13 |
| filtrate (g.) | 25 |
| Yield of later fraction (g.) | 8 |

TABLE 3-3

(Second reaction)

| | |
|---|---|
| Amount of benzene (g.) | 3.3 |
| Amount of redives (g.) | 47 |
| Condition of reaction: | |
| Amount of aluminum chloride(initial one + additional one) (g.) | 0.2 + 15 |
| Addition of $Br_2$ (g.) | 20 g. |
| Temperature (°C.) | 80–100° C. |
| Time for addition (hr.) | 1 hr. |
| Temp. for heating (°C.) | 130 to 135° C. |
| Reaction time from addition of $Br_2$ (hour) | 3 |

TABLE 3-4

(Second reaction)

| | |
|---|---|
| Crude oily product | |
| Yield (g.) | 58 |
| Composition (%) | |
| 1,3,5-TBB | 33.0 |
| 1,2,4-TBB | 32.1 |
| 1,2,3-TBB | 0.5 |
| MBB | 0.4 |
| DBB | 20.4 |
| TEBB | 13.6 |
| Yield of Initial fraction (g.) | 11 |
| Yield of main fraction | |
| 1,3,5-TBB (g.) | 13 |
| filtrate (g.) | 24 |
| Yield of later fraction (g.) | 7 |

Vapor phase chlorination step:

In the reactor of Example 1, 2.0 mol of chlorine gas preheated at 300° C. was fed through a preheating tube and a solution of 1 mol of 1,3,5-tribromobenzene in 7 mol of carbon tetrachloride was heated at 300° C. to vaporize it and the vaporized mixture was fed through the other preheating tube into the reaction tube to react them at 340° C. The residence time of the reaction mixture in the reaction tube was about 60 seconds.

The gaseous reaction mixture discharged from the reaction tube was purified as the process of Example 1 to obtain a solid product. According to a gas chromatography analysis, the solid product contains 87.1% of 1,3,5-trichlorobenzene, 7.5% of 1-bromo-3,5-dichlorobenzene 3.9% of 1-chloro-3,5-dibromobenzene and 0.9% of 1,3,5-tribromobenzene.

REFERENCES 1 and 2:

In the reactor of Example 1, monochlorobenzene (MCB) or m-dichlorobenzene (m-DCB) was chlorinated at 450° C. in a vapor phase for a residence time of 10 seconds. The reaction is to substitute hydrogen atom on benzene ring by chlorine atom and it is different from the reaction for substituting bromine atom by chlorine atom in the process of the present invention.

In the chlorination of monochlorobenzene, monochlorobenzene, chlorine and nitrogen at molar ratios of 1:2:5 were fed.

In the chlorination of m-dichlorobenzene, m-dichlorobenzene, chlorine and nitrogen at molar ratios of 1:0.5:5 were fed.

The reaction mixtures obtained by collecting each gaseous product discharged from the reaction tube were analyzed by a gas chromatography analysis. The results are shown in Table 4.

TABLE 4

| | Ref. 1 | Ref. 2 |
|---|---|---|
| Starting material | MCB | m-DCB |
| Composition of reaction mixture: | | |
| MCB | 2.1 | — |
| DCB | 31.3 | m-DCB 46.2 |
| 1,3,5-TCB | 22.4 | 32.5 |
| 1,2,4-TCB | 24.5 | 14.4 |
| 1,2,3-TCB | 4.2 | 1.4 |
| tetrachlorobenzene | 15.1 | 5.4 |

We claim:

1. In a process for producing 1,3,5-trichlorobenzene by chlorinating 1,3,5-trihalobenzene having 1 to 3 bromine atoms and 2 to 0 chlorine atoms, an improvement characterized in that gaseous 1,3,5-halobenzene having 1 to 3 bromine atom and 2 to 0 chlorine atom is brought into contact with chlorine gas at a molar ratio of 0.5 to 3.0 of the stoichiometric amount of chlorine required for said conversion, in a vapor phase at a temperature of 280° to 500° C.

2. The process according to claim 1 wherein the said 1,3,5-trihalobenzene is 1-bromo-3,5-dichlorobenzene.

3. The process according to claim 1 wherein the reaction is carried out at a temperature of 300°–400° C.

4. The process according to claim 1 wherein the reaction is carried out, with chlorine gas at a molar ratio of 0.8 to 2.0 of the stoichiometric amount of chlorine required for said conversion.

5. The process according to claim 1 which comprises reacting 1-bromo-3,5-dichlorobenzene with chlorine gas at a molar ratio of 0.8 to 2.0 of the stoichiometric amount of chlorine required for said conversion in the vapor phase and at a temperature of 300° to 400° C.

6. The process according to claim 1 wherein said reaction is followed by the steps comprising cooling the gaseous product and distillating the product to distillate off bromine to obtain the 1,3,5-trichlorobenzene.

* * * * *